United States Patent [19]

Mattout

[11] Patent Number: 4,643,021
[45] Date of Patent: Feb. 17, 1987

[54] METHOD AND APPARATUS FOR MEASURING THE RHEOLOGICAL CHARACTERISTICS OF A FLUID, IN PARTICULAR OF A BIOLOGICAL FLUID SUCH AS BLOOD

[75] Inventor: Richard Mattout, Saint-Cloud, France

[73] Assignee: Bertin & Cie, Plaisir, France

[21] Appl. No.: 790,186

[22] Filed: Oct. 22, 1985

[30] Foreign Application Priority Data

Oct. 30, 1984 [FR] France .................... 84 16603

[51] Int. Cl.$^4$ ............................ G01N 11/16
[52] U.S. Cl. ...................................... 73/59
[58] Field of Search ........................ 73/60, 59

[56] References Cited

U.S. PATENT DOCUMENTS

| | | | |
|---|---|---|---|
| 2,603,087 | 7/1952 | Von Hortenau | 73/59 |
| 3,053,078 | 9/1962 | Jewett | 73/54 |
| 4,152,927 | 5/1979 | Feng et al. | 73/60 |
| 4,299,119 | 11/1981 | Fitzgerald et al. | 73/59 |
| 4,499,753 | 2/1985 | Carr | 73/59 |

FOREIGN PATENT DOCUMENTS

| | | | |
|---|---|---|---|
| 1184119 | 2/1960 | Fed. Rep. of Germany | 73/59 |
| 1244408 | 9/1971 | United Kingdom | 73/59 |
| 518695 | 8/1976 | U.S.S.R. | 73/59 |
| 568869 | 8/1977 | U.S.S.R. | 73/60 |
| 819627 | 4/1981 | U.S.S.R. | 73/59 |

OTHER PUBLICATIONS

Hodgins, M. G. et al, *Magnetic Densimeter-Viscometer*, in Rev. Sci. Instr., vol. 42 (10), pp. 1455-1457, Oct. 1971.

*Primary Examiner*—Stewart J. Levy
*Assistant Examiner*—Joseph W. Roskos
*Attorney, Agent, or Firm*—Dennison, Meserole, Pollack & Scheiner

[57] ABSTRACT

The invention relates to a method and to a device for measuring, e.g. the viscosity of a fluid, by means of a rotating cylinder immersed in the fluid and on the basis of a torque applied to the cylinder and the cylinder's speed of rotation. The rotary cylinder (50) is completely immersed in the fluid contained in a tube (40) which is itself placed inside a constant temperature jacket (38) and is rotated by a rotating electromagnetic field produced by an induction winding (64) coaxially surrounding the tube and the cylinder and powered with alternating current at an adjustable predetermined intensity. The invention is applicable to measuring the viscosity of biological fluids, such as blood.

13 Claims, 3 Drawing Figures

METHOD AND APPARATUS FOR MEASURING THE RHEOLOGICAL CHARACTERISTICS OF A FLUID, IN PARTICULAR OF A BIOLOGICAL FLUID SUCH AS BLOOD

The invention relates to a method and to apparatus for measuring the rheological characteristics of a fluid, in particular the viscosity of a biological fluid such as blood.

BACKGROUND OF THE INVENTION

There are many varieties of rheometer which are of the rotary type comprising a fixed cylinder containing the fluid and a cylindrico-conical element which is dipped into the fluid and which has a torque applied thereto. By taking measurements of the torque applied to this element and of its speed of rotation about its axis, it is possible to determine the shear stress to which the fluid in contact with the rotary element is subjected, and the shear speed of the fluid at the wall of said element, and thus to determine the viscosity of the fluid which is the ratio between the shear stress and the shear speed. It is also possible to determine the manner in which the viscosity varies as a function of variations in the shear stress applied to the fluid.

Further, by measuring the axial force it is possible to establish other rheological characteristics (in viscoelasticity, for example).

In some cases, and in particular when the fluid is blood or a biological fluid, the speed at which the moving element is rotated must be very low, for example about one revolution in several minutes, and it is thus very difficult to measure the torque and the speed of rotation of the moving element with sufficient accuracy, unless very sophisticated and very expensive apparatus is used. Such apparatus is generally reserved for use by top level specialists. Making measurements with such apparatus takes a long time and can be very difficult, in particular because the rotary element is only partially dipped into the fluid and because surface tension forces where the rotary passes through the free surface of the fluid spoil the measurements. Further, when the fluid is blood, coagulation causes a skin to form on the surface, and since the rotary element passes through this skin, measurements are also spoiled by the skin. It is generally the case that the rotary element is guided in rotation about its axis by a mechanical device, which thus has contact friction with a prortion of the rotary element, thereby further spoiling the measurements, even if only to a small extent.

Viscosity meters are also known in which the moving element is kept completely immersed in the fluid, in order to avoid some of the above-mentioned drawbacks. However, in such apparatus, speed measurements must take a very long time in order to be accurate and this gives rise to other difficulties, for example settling phenomena may take place in biological fluids.

These known viscosity meters or rheometers are thus not reliably usable by personnel having modest technical qualifications, for example by nurses or laboratory assistants in clinics, hospitals, medical analysis laboratories, etc.

Preferred embodiments of the present invention provide a high precision rheometer which avoids the drawbacks of prior apparatus and which can be used simply, quickly and safely by personnel having modest technical qualifications.

SUMMARY OF THE INVENTION

The present invention provides a method of measuring the rheological characteristics of a fluid, in particular the viscosity of a biological fluid such as blood, the method consisting in applying a torque without contact to a cylinder which is completely immersed in the fluid and in determining the viscosity of the fluid from measurements of the torque and of the speed of rotation of the cylinder, the method including the improvement whereby the cylinder is caused to rotate about its axis by means of a rotating electromagnetic field produced by a winding which coaxially surrounds a tube containing the fluid together with the cylinder, and which is fed with an electric current of predetermined magnitude and at a non-zero frequency, in measuring the instantaneous speed of rotation of the cylinder, and in repeating this measurement at other values of torque applied to the cylinder.

Thus, the measurements of the torque applied to the cylinder and the measurements of its speed of rotation are not spoiled by the surface tension of the fluid where the cylinder passes through its free surface, nor by a modification of said free surface, nor by friction contact between the cylinder and the walls of the tube containing the fluid or between the cylinder and means for guiding rotation of the cylinder.

Further, it is the electrical current feeding the winding which determines the value of the torque applied to the cylinder, thus making it possible to measure the torque simply by measuring the electrical current (after a preliminary calibration). Measuring the instantaneous speed of rotation of the cylinder makes it possible to perform a plurality of measurements at several values of cylinder torque and thus to obtain a viscosity curve.

Preferably, the method consists in keeping the cylinder immersed by means of a magnetic or electromagnetic suspension field acting on the axial ends of the cylinder in such a manner as to prevent the, or each, end of the cylinder from coming into contact with the tube or with a guide device provided in the tube.

Advantageously, the tube containing the fluid and the rotary cylinder is itself placed in a constant temperature jacket in order to ensure that the measurements of fluid viscosity are not influenced by variations in the temperature of the fluid.

The rotary cylinder may be driven at extremely low speeds of rotation corresponding to shear speeds in the fluid which are very low, e.g. about $10^{-2} s^{-1}$ to $1 s^{-1}$.

This characteristic is particularly advantageous when the fluid whose viscosity is to be measured is blood.

The invention also provides a device for measuring the rheological characteristics of a fluid, such as its viscosity, in particular by performing the above-defined method, said device comprising a cylinder dipped in a fluid contained in a tube, together with means for applying a torque to the cylinder and for measuring the speed of rotation of the cylinder about its axis, the device including the improvement whereby the tube is made of non-magnetic material and is surrounded by a winding which is fed with electrical current at a predetermined intensity and at a non-zero frequency in order to produce a rotating electromagnetic field which acts on the cylinder to rotate it about its axis, magnetic and/or electromagnetic means being provided adjacent the axial ends of the cylinder to produce a magnetic and/or electromagnetic field for supporting the cylinder when dipped in the fluid in such a manner that, firstly the cylinder is completely immersed in the fluid, and secondly it does not come into friction contact with the tube containing the fluid, said device also including means for adjusting the current passing through the winding which produces the rotating electromagnetic field and means for measuring the instantaneous speed of rotation of the cylinder, thereby enabling a series of measurements to be made to determine the manner in which the viscosity of the fluid varies as a function of the torque applied to the rotary cylinder.

The device preferably also includes means for adjusting the intensity of the field which supports the cylinder dipped in the fluid.

It is then possible to adjust the cylinder-support field for a given fluid, thereby completely immersing the rotary cylinder in the fluid and avoiding any friction contact between the cylinder and the walls of the tube.

The density of the rotary cylinder may be less than or greater than the density of the fluid, and the cylinder is maintained fully immersed in the fluid by the support field.

Other rheological characteristics of the fluid may be obtained by measuring the axial displacement or the axial force on the rotary cylinder (e.g. viscoelastic characteristics).

The means for measuring the speed of rotation of the cylinder preferably comprise at least one proximity sensor, which is mounted in a fixed position facing a portion of the cylinder, which portion includes electrically-conductive regions which are regularly distributed around the periphery of the cylinder.

It is thus possible to measure extremely low speeds of cylinder rotation in a manner which is accurate and quick.

The proximity sensor is advantageously of the capacity type and comprises, for example, n metal regions mounted on a fixed cylindrical envelope which coaxially surrounds the tube containing the fluid and the rotary cylinder, said envelope being level with a different number of metal regions mounted on the rotary cylinder.

The accuracy with which the instantaneous speed of rotation of the cylinder is measured is thus increased by simplifying the structure of the measuring sensor and while reducing the space it occupies.

Preferably, a device in accordance with the invention is associated with programmed control and operating circuits which are suitable for controlling the production of the rotating electromagnetic field and of the field for supporting the rotary cylinder, which are suitable for verifying whether the speed of rotation of the cylinder is constant prior to taking a measurement, which are suitable for varying the electrical current producing the rotating electromagnetic field in a predetermined manner, which are suitable for storing pairs of measured values of current intensity and cylinder speed of rotation, and which are suitable for converting said stored pairs, by means of calibration curves, into pairs of values corresponding to shear stress and to shear speed in the fluid.

Thus, by reducing initial adjustments to a minimum, it is possible to perform a series of measurements enabling a curve to be plotted showing the variation of viscosity as a function of shear stress in the fluid.

Such a device operates in a substantially automatic manner and may be used without difficulty by personnel having modest technical qualifications.

BRIEF DESCRIPTION OF THE DRAWING

An embodiment of the invention is described by way of example with reference to the accompanying drawing, in which.

MORE DETAILED DESCRIPTION

Figure 1:
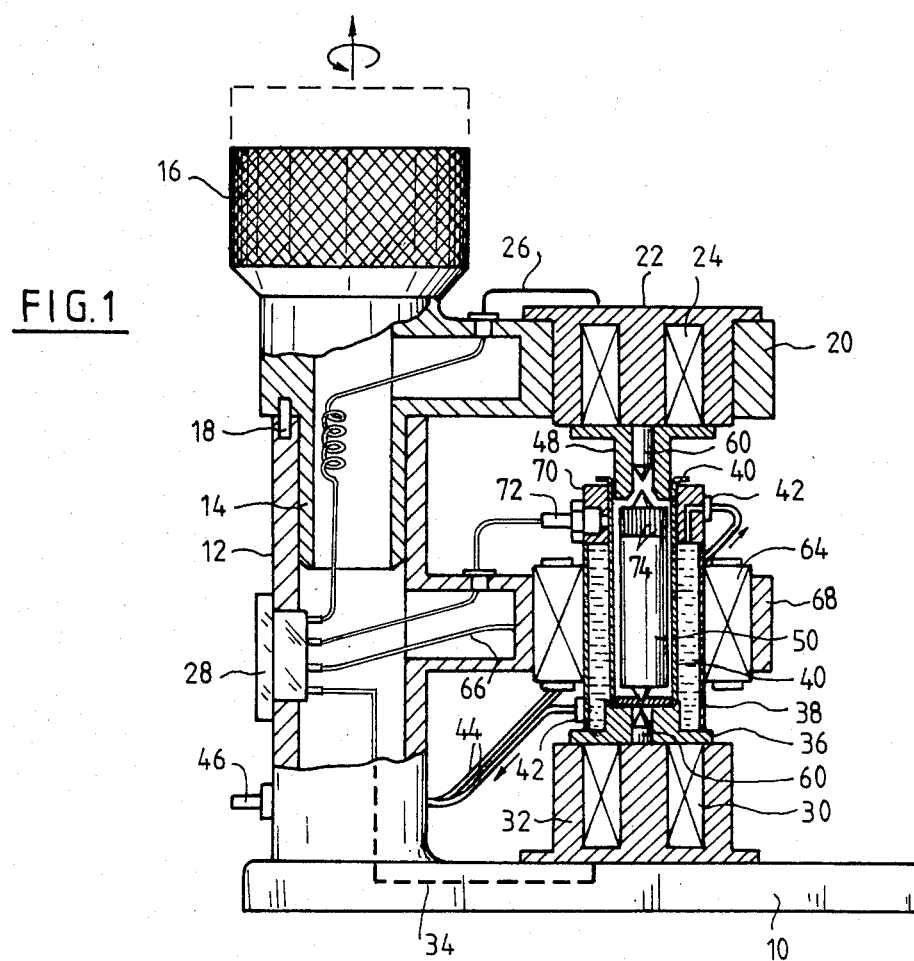
FIG. 1 is a diagrammatic axial section through a portion of a device in accordance with the invention.
Figure 3:
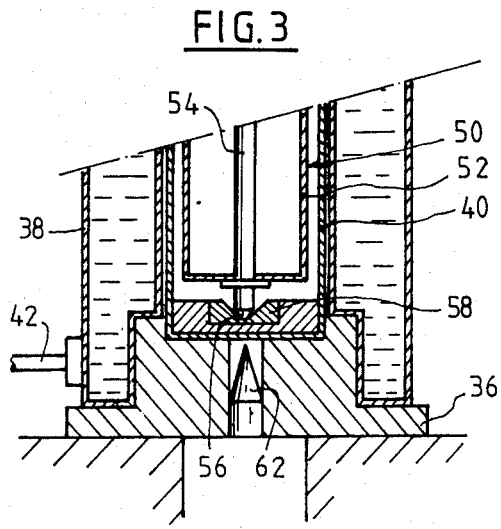
FIG. 3 is a diagrammatic view of a portion of the device shown in section on a line III—III of FIG. 2.
Figure 2:
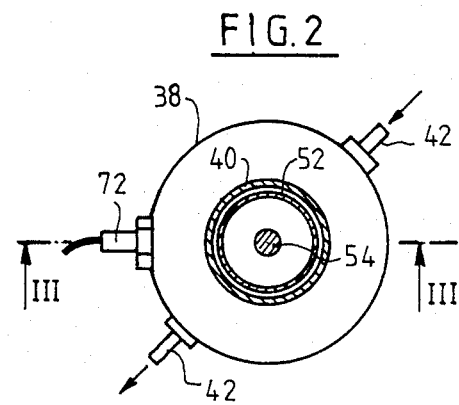
FIG. 2 is a diagrammatic cross-section through a portion of said device.

The device shown in FIG. 1 comprises a stand 10 provided with a vertical tubular riser 12 in which a vertical tubular arm 14 of a bracket 16 is engaged. The bracket 16 may be displaced relative to the vertical riser 12 in translation along a vertical axis and in rotation about said axis, with means such as a pin or peg 18 being provided to ensure that the bracket 16 takes up a predetermined angular position relative to the riser 12.

The horizontal arm 20 of the bracket 16 supports the core 22 of an induction winding 24 which is fed with electrical current via conductors 26 which pass inside the arms of the bracket and which are connected to a connection box 28 provided on the vertical riser 12.

In the predetermined angular position of the bracket 16 relative to the vertical riser 12 and the stand 10, the winding 24 and its core 22 are vertically aligned with a winding 30 whose core 32 is supported by the stand 10. The winding 30 is fed with electrical current via conductors 34 which likewise terminate at the connection box 28 on the vertical riser 12.

A base 36 of electrically-insulating and non-magnetic material is placed on the winding 30 and its core 32, the base 36 may be made of plastics material for example, and it supports, around its periphery, the bottom end of a tubular cylindrical jacket 38, and in the middle it supports the bottom end of a tube 40 having an open top end which is intended to contain the fluid 11 whose viscosity is to be measured.

The tubular jacket 38 is made of non-magnetic and electrically insulating material, e.g. a plastics material, and it has a permanent flow of constant temperature liquid, e.g. water, passing therethrough. For this purpose, the top and bottom ends of the jacket 38 are provided with fittings 42 which are connected via flexible ducts 44 to means 46 for connection to a constant temperature liquid circuit, the means 46 being provided on the vertical riser 12 of the device.

The tube 40 is placed inside the jacket 38 substantially in contact with the inside wall of the jacket, and it extends slightly above the top end thereof. The tube 40 is made of non-magnetic and electrically-insulating material, e.g. plastics material or glass, and its top end is held by a centering piece 48 made of non-magnetic and electrically-insulating material, which piece is fixed underneath the winding 24 and its core 22 as carried by the horizontal arm 20 of the bracket 16.

The tube 40, in addition to containing the fluid whose viscosity is to be measured, contains a cylinder 50 which is disposed coaxially inside the tube 40 and which comprises a cylindrical tubular envelope 52 made of non-magnetic and electrically-insulating material with closed ends, and has a cylindrical rod 54 of material having magnetic properties, e.g. soft iron, which rod extends over the full height of the cylinder 50 and passes in sealed manner through the closed ends of the tubular envelope 52.

The bottom end of the rod 54 terminates in a ball 56 of very hard material, e.g. iridium, which is received in a cup 58 disposed at the bottom of the tube 40.

The ends of the rod 54 are disposed opposite pole pieces 60 and 62 associated with respectives ones of the windings 24 and 30 and which are axially housed in respective centering pieces 48 and 36.

The jacket 38 is coaxially surrounded by an induction winding 64 which is fed with AC by conductors 66 which are terminated in the connection box 28. The winding 64 is mounted on a horizontal arm 68 which is fixed to the vertical riser 12.

As shown in FIG. 1, the top of the jacket 38 may comprise a cylindrical ring 70 of non-magnetic and electrically-insulating material comprising at least one radial housing in which a proximity sensor 72 is mounted and is likewise connected to the connection box 28. The sensor 72 detects the passage of electrically-conductive metal regions 74 provided at the top end of the envelope 52 of the rotary cylinder 50 and regularly distributed around the cylindrical periphery of said envelope.

The proximity sensor 72 may, for example, be of the capacitive type and may itself be constituted by a series of electrically-conductive metal regions which are regularly distributed around the inside periphery of the ring 70. In this case, the ring 70 may have n metal regions while the top end of the rotary cylinder 50 may have n+1 or n−1 conductive regions, for example. When the conductive regions of the rotary cylinder are connected in parallel to a conductive ring of the cylinder and when the conductive regions of the ring 70 are connected in series with one another and with a terminal of an electrical power supply whose other terminal is connected to a circular conductive track surrounding the conductive ring of the rotary cylinder and at a distance therefrom, rotation of the cylinder provides a sinusoidal signal whose frequency corresponds to the speed of rotation of the rotary cylinder.

The above-described device is used as follows:

A tube 40 containing the fluid whose viscosity is to be measured (e.g. blood or some other biological fluid) is placed inside the jacket 38. The cylinder 50 whose density may be greater than the density of the fluid, for example, is placed inside the tube and is completely immersed in the fluid. The ball 56 at the bottom end of the rod 54 of the cylinder is thus received in the cup 58 at the bottom end of the tube 40. A flow of constant temperature liquid through the jacket 38 keeps the temperature of the tube 40, of the fluid therein, and of the cylinder 50 at a constant value.

The winding 64 is fed with AC, e.g. from a low frequency generator which includes means for regulating the intensity of the current supplied. The winding 54 produces a rotating electromagnetic field which is applied to the rod 54 made of soft iron or similar material within the rotary cylinder 50. A rotary torque is thus applied to the cylinder about its vertical axis. The intensity of the feed current to the winding 64 determines the value of the torque, and the frequency of this current is chosen to have some non-zero value.

The windings 24 and 30 are also fed with electrical current and, via their pole pieces 60 and 62, they provide an electromagnetic support field which is applied to the pointed ends of the rod 54 of the rotary cylinder 50. The effect of this electromagnetic field is to lift the bottom end of the rod 54 away from the cup 58, while still keeping the cylinder 50 completely immersed in the fluid.

The speed of rotation of the cylinder is measured by means of the proximity sensors 72. When this speed of rotation is constant, for a given intensity of current feed to the winding 64, the values of the speed of rotation and current intensity are noted. Calibration curves make it possible to convert these measurements into values for the fluid shear speed and for the fluid shear stress. These two values are used to obtain a value for the viscosity of the fluid.

Since this viscosity is not constant as a function of the shear stress, the value of the current intensity fed to the winding 64 is varied and a new measurement is made of the speed of rotation of the rotary cylinder, in order to obtain a new value for the viscosity. It is thus possible to make a point-by-point plot of the curve showing variation of viscosity as a function of variations in fluid shear stress.

By way of numerical example, assume that the rotary cylinder has an outside diameter of about one centimeter, that it is three to four centimeters long, and that it weighs three to four grams. The annular cylindrical space between the rotary cylinder and the tube 40 has a radial extent of about 1 mm. It will be understood that a relatively small amount of fluid needs to be placed in the tube 40. The speed of rotation of the cylinder 50 is about 1 revolution per minute, for example, which corresponds to fluid shear speeds of less than $1 \text{ s}^{-1}$.

Generally speaking, the device in accordance with the invention can be used to measure shear speeds lying in the range $10^3 \text{ s}^{-1}$ and $10^{-2} \text{ s}^{-1}$.

Once a series of measurements for a given sample of fluid has been completed, the tube 40 is removed from the jacket 38 and another tube may be inserted in its place containing another sample of fluid and another rotary cylinder.

Advantageously, a device in accordance with the invention is associated with programmed control circuits which enable the above-described sequence of operations and measurements to be performed automatically or substantially automatically. For example, these circuits may perform the following functions:

supply currents to the winding 63 and to the windings 24 and 30, check that the rotary cylinder is properly supported and that it is completely immersed in the fluid, check the speed of rotation of the cylinder;

vary the intensity of the current fed to the winding 64 in accordance with a predetermined plan, and note the pairs of measured values of current and of cylinder rotation speed; and convert the measured current intensity into shear stresses and convert the measured speeds of rotation into shear speeds, using calibration curves recorded in memory, and then print out the corresponding results or plot the corresponding curve showing variation of fluid voscosity.

Other variants or modifications may be applied to the device as described above and without going beyond the scope of the invention. For example, the density of the rotary cylinder may be less than the density of the fluid contained in the tube 40. In this case, the rotary cylinder would tend to float in the fluid and is kept immersed in suspension in the fluid by the electromagnetic field produced by the windings 24 and 30 and by their pole pieces 60 and 62.

The cylinder-supporting field may be produced magnetically or electromagnetically, by a combination of permanent magnets and induction windings, and it may be variable. It may also be produced, in some cases, solely by means of permanent magnets.

Further, a device in accordance with the invention could be disposed horizontally instead of being disposed vertically as shown in FIG. 1. In this case, the windings 24 and 30 would be horizontally-aligned, the jacket 38 would have a horizontal axis, and the tube 40 placed within the jacket would need to be hermetically sealed at both ends and completely filled with fluid.

Other means for measuring the speed of rotation of the cylinder 50 could likewise be used, provided they are sufficiently accurate when measuring small speeds of rotation.

The rotary element need not necessarily be cylindrical, and it could have any other shape, for example it could be cylindrico-conical, depending on the rheological characteristics to be measured.

Generally speaking, the method and the apparatus according to the invention enable accurate measurements to be taken of the viscosity of any fluid, with an accuracy that is better than 1% and at a relatively low price for the equipment.

I claim:

1. In a method of measuring the rheological characteristics of a fluid, in particular the viscosity of a biological fluid such as blood, by applying, without contact, a torque to a cylinder which is completely immersed in the fluid, and determining the viscosity of the fluid from measurements of the torque and of the speed of rotation of said cylinder, the improvement comprising the steps of:
   (a) maintaining said cylinder immersed and suspended in the fluid by means of a magnetic or electromagnetic cylinder-supporting field acting on the axial ends of said cylinder in such a manner as to prevent the ends of said cylinder from contacting said tube;
   (b) driving the cylinder to rotate by means of a rotating electromagnetic field produced by a winding which coaxially surrounds a tube containing the cylinder and the fluid;
   (c) providing the winding with electric current of non-zero frequency;
   (d) varying the magnitude of said electric current to produce a plurality of values of torque on said cylinder; and
   (e) measuring the instantaneous speed of rotation of the cylinder for each value of torque.

2. A method according to claim 1, wherein the tube containing the fluid and the cylinder are placed within a constant temperature jacket.

3. A method according to claim 1, wherein the cylinder is rotated at very slow speeds corresponding to very low fluid shear speeds, of about $1\ s^{-1}$ to $10^{-2}\ s^{-1}$.

4. A method according to claim 1, wherein the density of the rotary cylinder is less than the density of the fluid, and the cylinder is kept immersed in the fluid by the cylinder-supporting field.

5. A method according to claim 1, wherein the density of the cylinder is greater than the density of the fluid, and the cylinder is supported in the fluid contained in the tube by the cylinder-supporting field.

6. In a device for measuring the rheological characteristics of a fluid, such as its viscosity, the device comprising a tube for holding the liquid, and a rotatable cylinder contained axially within said tube, and which can be immersed in the liquid, the improvement comprising:
   (a) a winding coaxially surrounding said tube;
   (b) a source of electric current of non-zero frequency and variable magnitude connected to said winding, said current acting on said winding to produce a rotating magnetic field which acts on said cylinder to rotate it about its axis, and provide a torque on said cylinder depending on the magnitude of the electric current;
   (c) magnetic means level with each end of said cylinder for producing a magnetic cylinder supporting field which enables the cylinder to be completely immersed and suspended in the fluid, without coming into frictional contact with the tube; and
   (d) means for measuring the instantaneous speed of rotation of the cylinder.

7. A device according to claim 6, including means for adjusting the field which supports the cylinder immersed in the fluid.

8. A device according to claim 6, wherein the rotary cylinder comprises a hollow cylindrical envelope made of non-magnetic material and closed at its ends, and an axial rod made of magnetic material which passes in sealed manner through the ends of said envelope.

9. A device according to claim 8, wherein the axial rod of the cylinder is terminated at its bottom end by a ball suitable for being received in a cup at the end of a tube, when the cylinder comes to rest.

10. A device according to claim 6, wherein the tube containing the fluid and the rotary cylinder is placed in a jacket through which a constant temperature liquid is caused to flow.

11. A device according to claim 6, wherein the means for measuring the speed of rotation of the cylinder comprises at least one proximity detector fixed level with a portion of the cylinder which includes electrically-conductive regions which are regularly distributed around the periphery of the cylinder.

12. A device according to claim 11, wherein the proximity detector is of the capacitive type and comprises a plurality of metal regions mounted on a cylindrical ring which is fixed coaxially around the tube containing the fluid and the rotary cylinder, and level with a different number of metal regions mounted on the rotary cylinder.

13. A device according to claim 6, wherein the device is associated with programmed control and operation circuits suitable for controlling the production of the rotating electromagnetic field and for controlling the production of the cylinder-supporting field, for checking whether the speed of rotation is constant prior to performing a measurement, for varying the intensity of the electric current producing the rotating electromagnetic field in accordance with a predetermined relationship, for storing pairs of measured values concerning the current intensity and the speed of rotation of the cylinder, and for converting said pairs of values, by means of calibration curves, into pairs of values concerning shear stress and shear speed in the fluid.

* * * * *